(12) United States Patent
Pearce

(10) Patent No.: US 9,498,362 B2
(45) Date of Patent: Nov. 22, 2016

(54) WEDGE WIRE FOR USE WITH A NARROWED BIFURCATION VESSEL

(71) Applicant: Colin Pearce, Saskatoon Saskatchewan (CA)

(72) Inventor: Colin Pearce, Saskatoon Saskatchewan (CA)

(*) Notice: Subject to any disclaimer, the term of this patent is extended or adjusted under 35 U.S.C. 154(b) by 0 days.

(21) Appl. No.: 13/770,182

(22) Filed: Feb. 19, 2013

(65) Prior Publication Data

US 2014/0236273 A1    Aug. 21, 2014

(51) Int. Cl.
*A61F 2/06* (2013.01)
*A61F 2/954* (2013.01)

(52) U.S. Cl.
CPC ..................................... *A61F 2/954* (2013.01)

(58) Field of Classification Search
CPC .. A61F 2/95; A61F 2/954; A61F 2002/9534; A61F 2/958

USPC ........ 600/585; 606/108, 159, 194; 623/1.11, 623/1.35

See application file for complete search history.

(56) References Cited

U.S. PATENT DOCUMENTS 5,465,733 A * 11/1995 Hinohara et al. ............. 600/585
2009/0216315 A1 * 8/2009 Schreck et al. ............. 623/1.35

* cited by examiner

*Primary Examiner* — Ashley Fishback
(74) *Attorney, Agent, or Firm* — The Marbury Law Group, PLLC

(57) ABSTRACT

A wedge wire for maintaining the patency of an opening to a branch vessel while installing a stent in a main branch of a narrowed bifurcated vessel is provided. The wedge wire has a wedge portion that is larger than the rest of the body of the wedge wire and this wedge portion is used to maintain patency of the branch vessel when a balloon catheter is used to expand a stent in the main branch across the opening of the second branch.

8 Claims, 4 Drawing Sheets

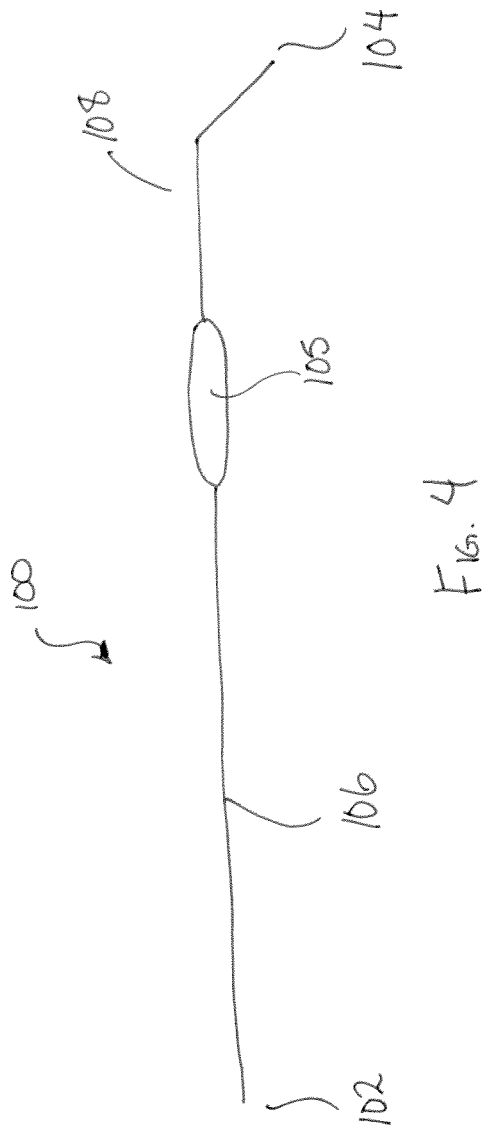
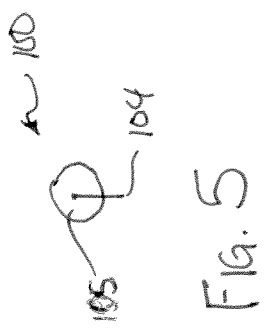
Fig. 4
Fig. 5

WEDGE WIRE FOR USE WITH A NARROWED BIFURCATION VESSEL

The present invention relates to a guide wire system for placing a stent at a vessel bifurcation.

BACKGROUND

Coronary arteries can become narrowed over time, such as when a build up of cholesterol and cellular debris causes a plaque to form. These narrowed vessels are commonly treated with the use of a stent to rexpand the vessel lumen. These stents are typically metal, meshlike and tubular in shape and can be expanded from a collapsed position on a balloon to an expanded position in the vessel when deployed. Typically, the stent is inserted through a vessel in its collapsed position until the stent reaches the location where the narrowing of the vessel occurs. Once at the desired location, the stent can be expanded by expanding the balloon to force open the vessel, allowing blood to continue to flow through the vessel. The stent acts as scaffolding to overcome the elastic recoil of the vessel wall and becomes incorporated into the vessel wall when a new lining grows over it. Typically, the stent is moved to the site in question, crimped on a balloon catheter. The balloon catheter is then inflated to expand the stent.

This method is used when the narrowing occurs along the main vessel or branch of the main vessel. However, when the narrowing occurs where one vessel branches away from another (a bifurcation), this presents additional challenges and requires additional techniques to be used to deal with the narrowing. One of these techniques is what is commonly referred to as the "kissing balloon" technique. It involves placing a stent in the main vessel so it runs across the opening to the branch vessel. Once the stent is in place, two guide wires can be placed (one in the main vessel, one partly down the main vessel, then down the branch vessel) with each guide wire having a balloon catheter running along each guide wire. Where the branch vessel opens into the main vessel, the balloons can be inflated, with one of the balloons used to further expand the stent, while the other balloon is used to balloon through the sidewall of the stent and into the branch vessel, maintaining its patency. However, this kissing balloon technique has its drawbacks. It typically results in damage to the vessel branching off the main vessel due to the expansion of the balloon against the branch vessel. This will increase the risk of renarrowing the side branch vessel in the weeks to months after the procedure.

SUMMARY OF THE INVENTION

In an aspect, a wedge wire, having a wedge that is larger than the body of the wedge wire is provided. The wedge of the wedge wire can be used to maintain patency of the branch vessel when the balloon placed on the first guide wire sitting in the main branch of the vessel is inflated within the stent and used to enlarge the stent.

In another aspect, a wedge wire for maintaining the patency of an opening to a branch vessel while installing a stent in a main branch of a narrowed bifurcated vessel is provided. The wedge wire comprises: a proximate end and a distal end; a wedge portion positioned proximate the distal end; a first portion extending between the proximate end and the wedge portion; and a distal portion extending between the distal end and the wedge portion. The wedge portion has a thickness that is greater than the thickness of the first portion and the thickness of the second distal portion.

In another aspect, a method of treating a narrowing of a bifurcated vessel, the bifurcated vessel having a main vessel, a branch vessel and an opening formed between the branch vessel and the main vessel is provided. The method comprises: deploying a stent in the main vessel across the opening to the branch vessel; using a first guide wire, positioning an uninflated balloon in the stent; providing a wedge wire having a proximate end and a distal end and a wedge portion proximate the distal end, the wedge portion having a thickness greater than the rest of the wedge wire; maneuvering the distal end of the wedge wire through a sidewall of the stent and through the opening into the branch vessel until the wedge portion of the wedge wire is positioned in the opening; and inflating the balloon to enlarge the stent while using the wedge portion of the wedge wire to maintain pendency in the opening.

DESCRIPTION OF THE DRAWINGS

A preferred embodiment of the present invention is described below with reference to the accompanying drawings, in which:

FIG. 4 illustrates a side view of a wedge wire;

FIG. 5 illustrates an end view of the wedge wire of FIG. 4;

DETAILED DESCRIPTION OF THE ILLUSTRATED EMBODIMENTS

Figure 1:
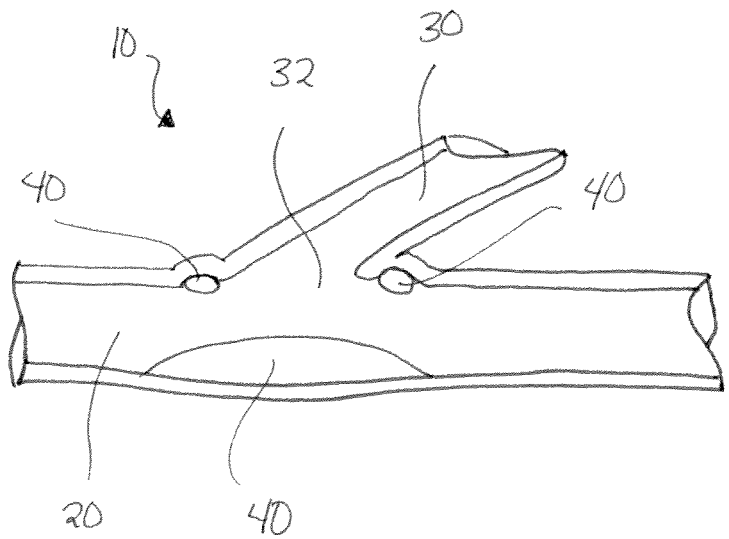
FIG. 1 is a schematic illustration of a narrowed vessel bifurcation.

FIG. 1 illustrates a vessel bifurcation 10 where a narrowing of the surrounding vessels has occurred, such as by the buildup of plaque, lesions, etc. Typically, the vessel bifurcation 10 can include a main vessel 20 with a branch vessel 30 having an opening 32 into the main vessel 20 and extending at an angle away from the main vessel 20. The main vessel 20 and the branch vessel 30 is a branch off of the main branch of the coronary artery.

The vessel bifurcation 10 also has a number of narrowings 40 located around the opening 32 of the branch vessel 30, formed by plaque, lesions, etc. that constrict flow through the main vessel 20. These narrowings 40 define a passage running through the narrowings 40 that is narrower than the main vessel 20.

Figure 2:
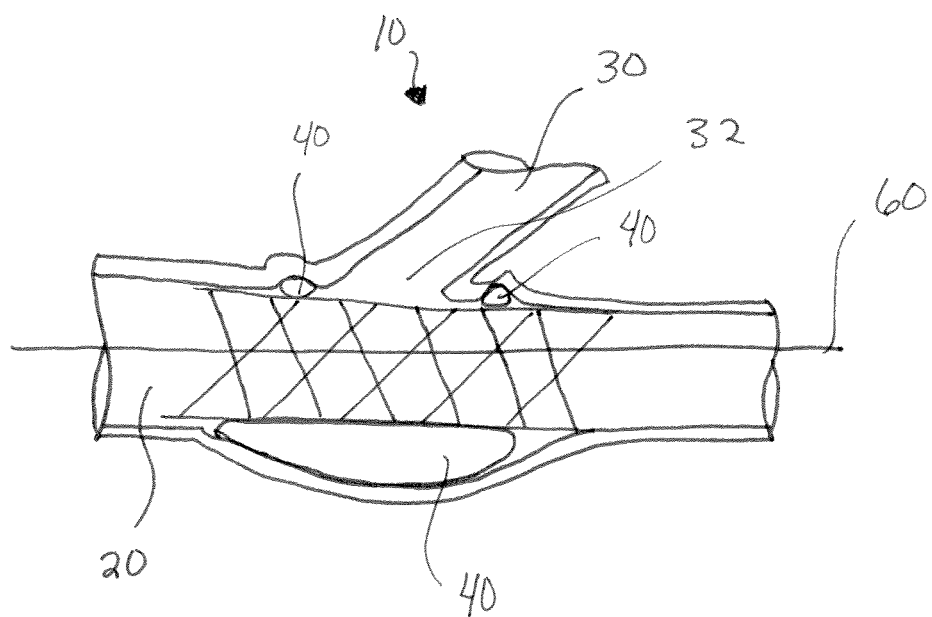
FIG. 2 is a schematic illustration of a prior art method where a stent is used in a first step of opening the narrowed vessel bifurcation.

FIG. 2 illustrates the first steps of a prior art method of opening the narrowed vessel bifurcation 10. A stent 50 can be inserted into the main vessel 20 so that it extends across the opening 32 of the branch vessel 30. Typically, a first guide wire 60 is used to position the stent 50 and balloon catheter (not shown) in place. The first guide wire 60 can be passed through the main branch 20 passing between the narrowings 40 and used to insert the stent 50 which would cross the opening 32 of the branch vessel 30. Typically, the walls of the branch vessel 30 become pinched close to the opening 32 of the branch vessel 30.

Figure 3:
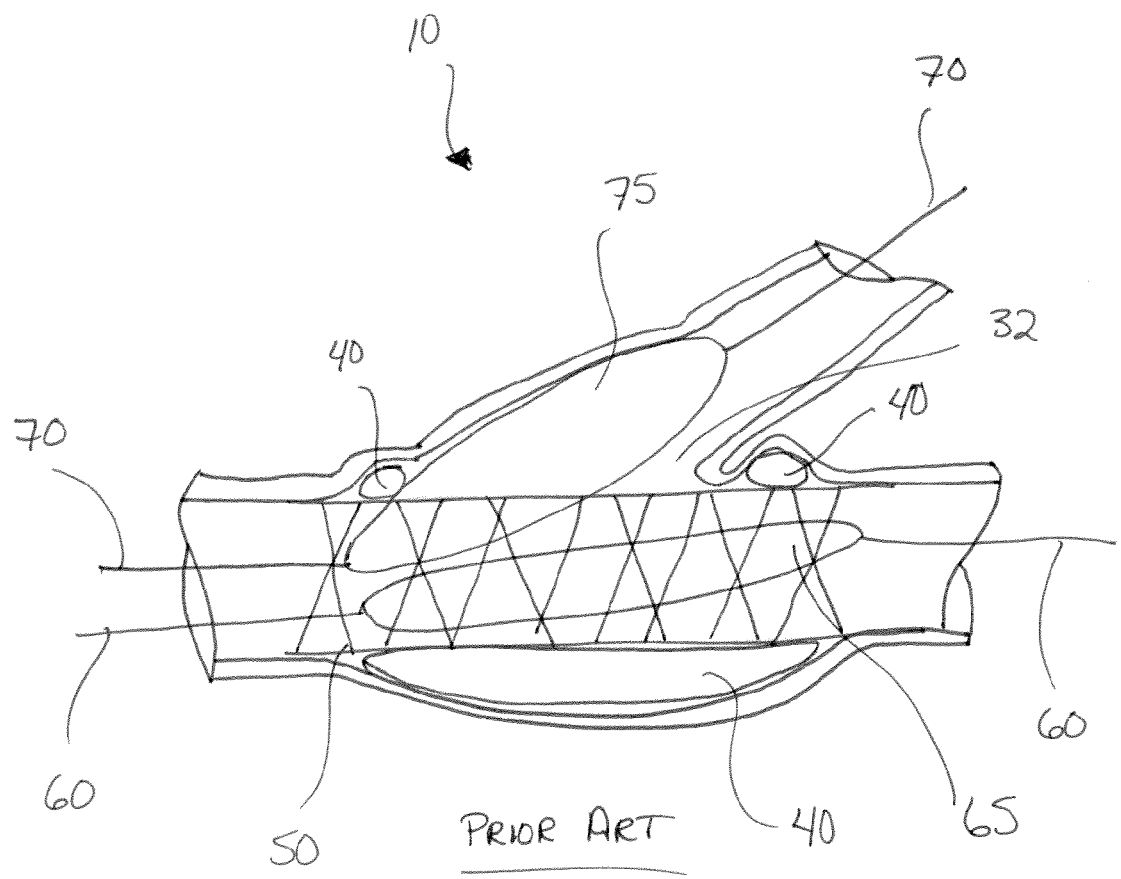
FIG. 3 is a schematic illustration of a "kissing balloon" technique as is used in the prior art.

FIG. 3 illustrates a "kissing balloon technique" as is commonly used in the prior art. After the stent 50 is inserted in the bifurcation vessel 100, a second guide wire 70 can be passed through the main vessel 20, through the side wall of the stent 50 at the opening 32 of the branch vessel 30 and into the branch vessel 30. A first balloon 65 can be advanced provided on the first guide wire 60 and positioned in the main branch so that it is placed within the stent 50 and an uninflated second balloon 75 can be positioned on the second guide wire 70 and guided so that it partially extends through the side wall of the stent 50 into the opening 30 of the branch vessel 30.

The second balloon 75 can be inflated simultaneously with the first balloon 65 on the first guide wire 60 being used to expand the stent 50. This maneuver will maintain patency of the main vessel 20, and the branch vessel 30.

However, this kissing balloon technique typically causes damage to the branch vessel 30 because the inflation of the first balloon 65 and the second balloon 75 can pinch the branch vessel 30 near the opening 32 of the branch vessel 30. In some cases, this damage could cause a nidus for neointimal hyperplasia (scarring) which may cause renarrowing of the branch vessel 30.

FIG. 5 illustrates a wedge wire 100 for use with a narrowed bifurcated vessel. Unlike conventional guide wires that have a relatively uniform diameter, the wedge wire 100 varies in thickness along a portion of its length. The wedge wire 100 can have a proximate end 102, used to feed the wedge wire 100 through a vessel, and a distal end 104, that is inserted into the vessel the wedge wire 100 is being fed through. The wedge wire 100 can also have a wedge portion 105 provided close to the distal end 104 of the wedge wire 100.

Figure 7:
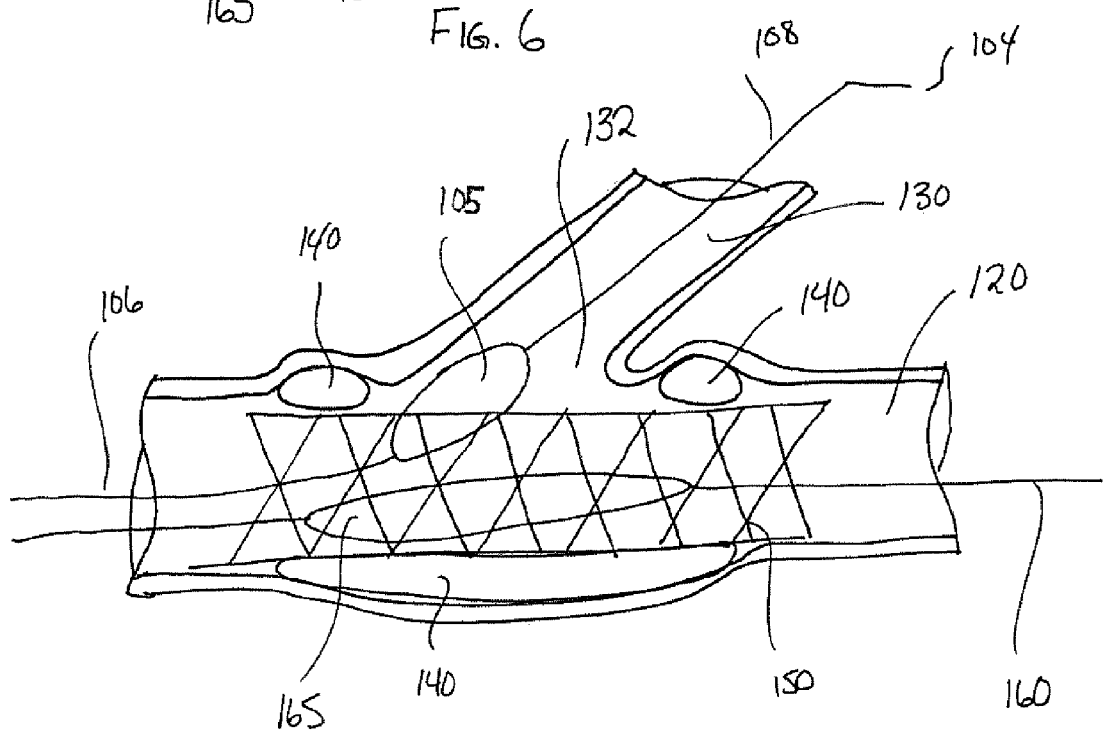
FIG. 7 illustrates a second step of the method first shown in FIG. 6.

The wedge wire 100 can have a first portion 106 that has a first thickness and/or diameter. The wedge portion 105 can have a second thickness and/or diameter that is larger than the first thickness and/or diameter of the first portion 106 of the wedge wire 100. A distal portion 108 can be provided between the distal end 104 of the wedge wire 100 and the wedge portion 105 of the wedge wire 100. The distal portion 108 can have a thickness and/or diameter that is smaller than the thickness and/or diameter of the wedge portion 105 of the wedge wire 100, which would be similar in diameter to the proximal portion of the first portion 106. As shown in FIG. 7, the wedge portion 105 is configured to connect the first portion 106 and the distal portion 108.

Although diameter is used to describe the cross-section of the wedge wire 100, a person skilled in the art would understand that the wedge wire 100 could have a cross-section that is not circular, such as elliptical, etc.

In various aspects, the wedge portion 105 of the wedge wire 100 could have various diameters of 0.5 mm, 1 mm, 1.5 mm, 2 mm, etc. In one aspect, the length of the distal portion 108 can be approximately 10 mm, making the wedge portion 105 of the wedge wire 100 approximately 10 mm from the distal end 104 of the wedge wire 100. The wedge portion 105 may be tapered at its ends so as to not catch on the meshwork of the stent as it passed through the stent sidewall.

Figure 6:
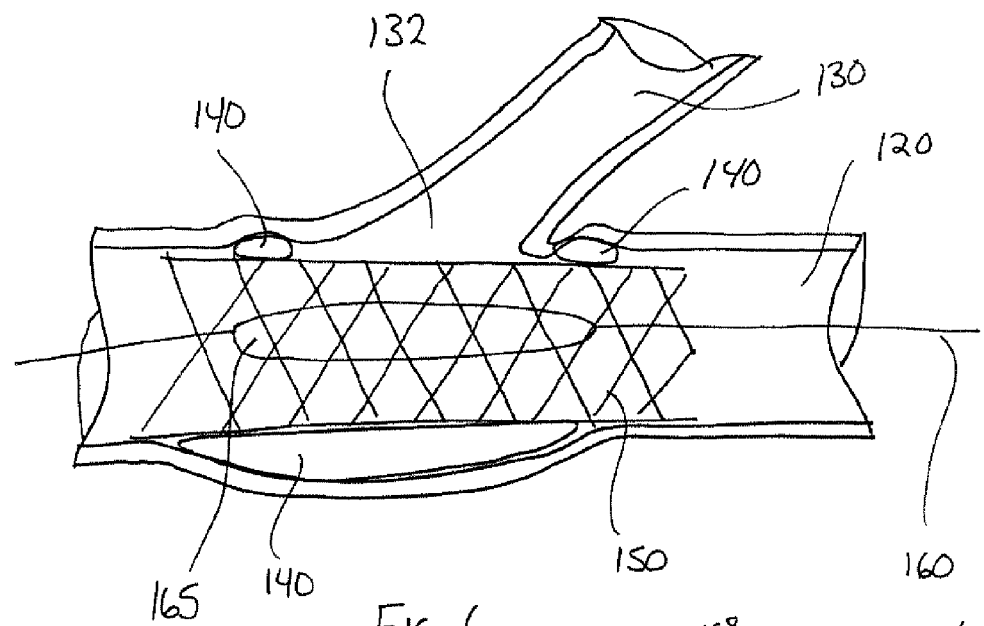
FIG. 6 illustrates a first step of a method for inserting a stent in a vessel bifurcation.

The wedge wire 100 can be used in conjunction with a stent to deal with a narrowing of a bifurcated vessel. FIG. 6 illustrates a first step of another method where a stent 150 is first deployed across the opening 132 of branch vessel 130 extending from a main vessel 120. Narrowings 140 are present in the main vessel 120. A first guide wire/balloon catheder 160 can be used to position the stent 150 in place.

FIG. 7 illustrates a second step of the method. The stent has now been deployed. The main branch guide wire 160 now has an uniflated balloon positioned on it (this in most cases is a new balloon and the initial balloon that had deployed the stent has been removed and replaced). The first guide wire 160 can be used to position the uniflated balloon 165 inside the stent 150. The distal end 104 of the wedge wire 100 can then be maneuvered up the main vessel 120 to the opening 32 of the branch vessel 130. At the opening 32, the distal end 104 of the wedge wire 100 can be inserted through a side wall of the stent 150 and through the opening 132 of the branch vessel 130 and into the branch vessel 130. The distal end 104 of the wedge wire 100 can be extended into the branch vessel 130 until the wedge portion 105 of the wedge wire 100 is positioned in the opening 32 of the branch vessel 130.

The wedge portion 105 of the wedge wire 100 can be used to maintain patency of the branch vessel 130 when the balloon 165 placed on the first guide wire 160 is inflated within the stent 150 and used to enlarge the stent 150. In this manner a second balloon catheter is not needed because the wedge portion 105 of the wedge wire 100 maintains patency of the opening 132.

Additionally, the wedge portion 105 of the wedge wire 100 could also be used to enlarge the opening in the sidewall of the stent 150, if needed.

The foregoing is considered as illustrative only of the principles of the invention. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention.

The invention claimed is:

1. A method of treating a narrowing of a bifurcated vessel, the bifurcated vessel having a main vessel, a branch vessel and an opening formed between the branch vessel and the main vessel, the method comprising:
   deploying a stent in the main vessel across the opening to the branch vessel;
   using a first guide wire, positioning an uninflated balloon in the stent;
   accessing a wedge wire having a first portion with a proximate end, a distal portion with a distal end, and a wedge portion proximate the distal end, wherein the wedge portion has a thickness greater than the rest of the wedge wire, and wherein the wedge portion is located between the first portion of the wedge wire and the distal portion of the wedge wire is configured to connect the first portion and the distal portion;
   maneuvering the distal end of the wedge wire through a sidewall of the stent and through the opening into the branch vessel until the wedge portion of the wedge wire is positioned in the opening; and
   inflating the balloon to enlarge the stent while using the wedge portion of the wedge wire to maintain pendency in the opening.

2. The method of claim 1 further comprising enlarging an opening in the sidewall of the stent using the wedge portion of the wedge wire.

3. The method of claim 1 wherein the first portion is configured to extend between the proximate end and the wedge portion and a distal portion is configured to extend between the distal end and the wedge portion, and wherein the thickness of the wedge portion is greater than the thickness of the first portion and a thickness of the distal portion.

4. The method of claim 3 wherein the thickness of the first portion of the wedge wire and the thickness of the distal portion of the wedge wire are substantially the same.

5. The method of claim 3 wherein the first portion, the wedge portion and the distal portion of the wedge wire have circular cross-sections.

6. The method of claim 5 wherein a diameter of the wedge portion is greater than 1.0 mm to 2 mm and a diameter of the first portion is less than 0.5 mm.

7. The method of claim 3 wherein the wedge portion of the wedge wire has tapered ends.

8. The method of claim 3 wherein the distal portion of the wedge wire has a length of 10 mm.

* * * * *